United States Patent [19]

Akiyama et al.

[11] Patent Number: 5,346,817
[45] Date of Patent: Sep. 13, 1994

[54] METHOD FOR PRODUCING A MICROBIAL POLYESTER

[75] Inventors: Minoru Akiyama; Yoshiharu Doi, both of Yokohama, Japan

[73] Assignee: Asahi Kasei Kogyo Kabushiki Kaisha, Osaka, Japan

[21] Appl. No.: 903,021

[22] Filed: Jun. 23, 1992

[30] Foreign Application Priority Data

Jun. 24, 1991 [JP] Japan ............................. 3-177721
Sep. 5, 1991 [JP] Japan ............................. 3-254199

[51] Int. Cl.$^5$ .................. C08G 63/06; C12P 7/62; C12R 1/05
[52] U.S. Cl. ..................... 435/135; 435/829; 528/361
[58] Field of Search ....................... 435/135, 829

[56] References Cited

U.S. PATENT DOCUMENTS

| | | | |
|---|---|---|---|
| 4,393,167 | 7/1983 | Holmes et al. | 525/64 |
| 4,477,654 | 10/1984 | Holmes et al. | 435/135 |
| 5,096,819 | 5/1992 | Page et al. | 435/135 |
| 5,126,255 | 6/1992 | Anderson et al. | 435/135 |

FOREIGN PATENT DOCUMENTS

57-150393  9/1982  Japan .

*Primary Examiner*—Herbert J. Lilling
*Attorney, Agent, or Firm*—Pennie & Edmonds

[57] ABSTRACT

An improved method for producing a microbial polyester comprising 3-hydroxybutyrate monomer units is disclosed, in which a strain belonging to the genus Alcaligenes is cultured in a liquid medium containing a carbon source selected from specific long chain fatty acids and derivatives thereof. The produced microbial polyester is useful in plastics and polymers which are free from environmental pollution problems, and in implanting materials and drug carriers, recovery of which is not necessary.

7 Claims, No Drawings

METHOD FOR PRODUCING A MICROBIAL POLYESTER

BACKGROUND OF THE INVENTION

1. Field of the Invention

The present invention relates to a method for producing a microbial polyester. More particularly, the present invention is concerned with a method for producing a microbial polyester comprising 3-hydroxybutyrate monomer units, in which a strain belonging to the genus Alcaligenes is cultured in a liquid medium. The microbial polyester produced is useful in plastics and polymers which are free from environmental pollution problems, and in implanting materials and drug carriers, recovery of which is not necessary.

2. Discussion of Related Art

Microbial polyesters, such as poly(3-hydroxybutyrate), which are produced by the biosynthetic function of a microorganism, are readily biodegraded by microorganisms and within the body of higher animals, including humans, whereas it is generally impossible to biodegrade petrochemically synthesized polymers. The poly(3-hydroxybutyrate) produced by the biosynthetic function of a microorganism is entirely composed of optically active D-(−)-3-hydroxybutyrate monomer units (optical purity 100%), and readily biodegraded. On the other hand, polymers entirely composed of optically active monomer units cannot be prepared by the present petrochemical technology, and polymers prepared by the present petrochemical technology are generally not biodegradable. In recent years, tremendous amounts of synthetic plastics and polymers have been used in various application fields, and tremendous amounts of used plastics and polymers have been piled as bulky undecayed waste. Pollution of the environment by such bulky undecayed waste is now a serious problem. The above-mentioned microbial polyesters are introduced in the ecosystem through biodegradation thereof, so that they are useful as plastics and polymers which are free from environmental pollution problems. Moreover, in the field of medicine, the microbial polyesters can be used as an implanting material and a drug carrier, recovery of which is not necessary.

It has been reported that a wide variety of bacteria produce poly(3-hydroxybutyrate) in their cells, accumulating the same in the form of particles (see H. Brandle et al., Adv. Biochem. Eng./Biotechnol., 41, pages 77–93, 1990). In particular, it has been reported that copolymers comprised of 3-hydroxybutyrate monomer units and 3-hydroxyvalerate monomer units or comprised of 3-hydroxybutyrate monomer units, 3-hydroxyvalerate monomer units and other monomer units are produced from a preselected water soluble carbon source, such as glucose, propionic acid, butyric acid, or combinations thereof, by the use of *Alcaligenes eutrophus* (see Japanese Patent Application Laid-Open Specification No. 57-150393/1982), strains belonging to any one of the genus Nocardia, the genus Corynebacterium and the genus Rhodococcus (see European Patent No. 396,289) and *Rhodospirillum rubrum* (see H. Brandl et al, Int. J. Biol. Macromol., 11, pages 49–55, 1989). Commercial use of the above-mentioned copolymers comprised of 3-hydroxybutyrate monomer units and 3-hydroxyvalerate monomer units is being promoted as a thermoplastic resin improved in hardness and brittleness as compared to those of poly(3-hydroxybutyrate).

SUMMARY OF THE INVENTION

In the current situation as described above, the present inventors have conducted extensive and intensive studies with a view toward developing an improved method for producing a microbial polyester comprising 3-hydroxybutyrate monomer units. As a result, it has been found that efficient production of such a microbial polyester can be achieved by culturing a strain belonging to the genus Alcaligenes in a liquid medium containing a specific water insoluble carbon source having a long carbon chain. The present invention has been made, based on this novel finding.

Accordingly, it is an object of the present invention to provide an improved method for producing a microbial polyester comprising 3-hydroxybutyrate monomer units.

It is another object of the present invention to provide a novel strain having an improved ability to produce such a microbial polyester.

The foregoing and other objects, features and advantages of the present invention will be apparent from the following detailed description and appended claims.

DETAILED DESCRIPTION OF THE INVENTION

In one aspect of the present invention, there is provided a method for producing a microbial polyester comprising 3-hydroxybutyrate monomer units, which is comprised of the following steps:

(1) culturing a strain belonging to the genus Alcaligenes and having the ability to produce a microbial polyester comprising 3-hydroxybutyrate monomer units in a liquid medium containing at least one essential carbon source selected from the group consisting of fatty acids each having 10 to 22 carbon atoms and derivatives thereof, thereby obtaining a cultured broth containing a microbial polyester comprising 3-hydroxybutyrate monomer units; and (2) isolating the microbial polyester from the cultured broth.

The terminology "3-hydroxybutyrate monomer unit" used herein means a monomer unit of D-(−)-3-hydroxybutyrate. For simplicity, the above terminology is employed herein.

In another aspect of the present invention, there is provided a novel species, *Alcaligenes lipolytica* (Fermentation Research Institute Accession No. FERM BP-3819) having the ability to utilize at least one member selected from the group consisting of fatty acids, fats and oils each having at least 10 carbon atoms to thereby produce a microbial polyester comprising 3-hydroxybutyrate monomer units, and being negative to both a nitrate reduction and a denitrification reaction.

In the measurement of the nitrate reduction, culturing is performed in a nitrate-containing bouillon, and a nitrate concentration is determined every day during a period of from the 2nd day to the 5th day after the start of the culturing. On the other hand, the denitrification reaction is performed according to the method of K. Komagata et al., J. Gen. Appl. Microbiol., 14, 19(1968), in which culturing is performed in a medium comprised of a bouillon containing 1% sodium nitrate, which medium has a surface covered with liquid paraffin, followed by analyses of turbidity and gas formation.

In the method of the present invention, use is made of strains belonging to the genus Alcaligenes and having the ability to produce a microbial polyester comprising 3-hydroxybutyrate monomer units. Representative examples of such strains are for example, of species *Alcaligenes faecalis, Alcaligenes denitrificans, Alcaligenes eutrophus, Alcaligenes paradoxus* and *Alcaligenes aquamarinus*. Particularly, strains belonging to the above species and having the ability to utilize (assimilate) at least one member selected from the group consisting of fatty acids, fats and oils each having at least 10 carbon atoms to thereby produce a microbial polyester comprising 3-hydroxybutyrate monomer units, and being negative to both a nitrate reduction and a denitrification reaction, are preferably employed. Most preferred is a strain found by the present inventors, designated as *Alcaligenes lipolytica* AK 201, deposited on Apr. 17, 1991 with the Fermentation Research Institute of the Agency of Industrial Science and Technology, and assigned Accession No. FERM BP-3819.

*Alcaligenes lipolytica* AK 201 has been discovered and isolated in the manner described below.

Passage-stored strain ATCC 29347 belonging to the genus Pseudomonas was cultured in a liquid medium to obtain a cultured broth. As a result, the cultured broth was contaminated with other bacteria. Hence, isolation of the strain was conducted according to the following procedure. That is, an aliquot of the cultured broth was subjected to quantitative dilutions (diluted in the range of from $10^5$-fold to $10^7$-fold) with sterilized water to obtain 7 levels of dilutions. Each of the dilutions was plate cultured on a petri dish to form colonies. From five colonies selected therefrom, strains were picked, and were separately subjected to culturing in a liquid medium. Each strain grown in the liquid medium was inoculated into a slant medium, cultured for 4 days and subjected to assay for determining bacteriological and chemotaxonomic properties.

All of the above-mentioned liquid medium and slant medium and the medium for the above-mentioned plate culturing were comprised of the fundamental inorganic medium having the composition shown in the following Table 1, to which sodium n-octanoate was added as a carbon source in a concentration of 2.5 g/liter.

To each of the slant medium and the medium for the plate culturing, agar was further added in a concentration of 15 g/liter.

TABLE 1

| Composition of Fundamental Inorganic Medium | |
|---|---|
| $(NH_4)_2HPO_4$ | 1.1 g |
| $K_2PHO_4$ | 5.8 g |
| $KH_2PO_4$ | 3.7 g |
| $MgSO_4$ | 0.12 g |
| Minor element solution* | 1 ml |
| Water | 1000 ml |

*The minor element solution is a solution obtained by dissolving in one liter of 1 M hydrochloric acid 2.78 g of $FeSO_4.7H_2O$, 1.98 g of $MnCl_2.4H_2O$, 2.81 g of $CoSO_4.7H_2O$, 1.67 g of $CaCl_2.2H_2O$, 0.17 of $CuCl_2.2H_2O$, and 0.29 g of $AnSO_4.7H_2O$.

Culturing was performed at a temperature of 30° C. for a period of 24 hours in the case of the culturing in the liquid medium and 4 days in the case of the plate culturing and the culturing in the slant medium.

As a result of the above-mentioned assays, it has been found that the strain designated as AK 201, which was derived from one colony, has bacteriological and chemotaxonomic properties as described below.

There was no significant difference in appearance between AK 201 and the strains derived from other colonies. However, a further study by means of an electron microscope showed that the flagella grown on strain AK 201 are not polar flagella characteristic of the genus Pseudomonas but peripheral flagella. Further study with respect to physiological properties showed that the results obtained are different in regard to at least five items [reduction of a nitrate salt, utilization of citric acid, urease, O(oxidation)-F(fermentation) test and utilization of glucose] among the assay items for physiological properties between strain AK 201 and the strains derived from other colonies. Hence, the taxonomic position of strain AK 201 was studied, and judged as belonging to the genus Alcaligenes.

In the assays of physiological properties, an oxidase test was performed by culturing in a bouillon containing 1% peptone and then observing coloring with a test paper. Further, an acid formation test from glucose was performed using aqueous peptone as a fundamental medium, and a utilization test of citric acid was performed using Koser, Simmons' and Christensen mediums. With respect to morphological characteristics, the conditions of grown flagella were observed by means of an electron microscope, and the other conditions were observed by means of an optical microscope according to the conventional procedure.

The bacteriological properties of the novel strain AK 201 are as follows.
(a) Morphology
  (1) Shape and size of cells: bacillus, 0.4–0.7×0.7–1.5 μm.
  (2) Polymorphism of cells: none.
  (3) Motility: positive.
  (4) Growth of flagella: peripheral flagella grown.
  (5) Spore: none.
  (6) Gram staining: negative.
(b) Growth State in Various Culture Mediums
  (1) Culturing in plate bouillon agar medium: white, grows well.
  (2) Culturing in slant bouillon agar medium: white, grows well.
  (3) Culturing in liquid bouillon medium: cream color, grows well.
(c) Physiological Properties
  (1) Reduction of a nitrate: negative.
  (2) Denitrification reaction: negative.
  (3) Formation of indole: negative.
  (4) Utilization of citric acid: positive.
  (5) Utilization of an inorganic nitrogen source: positive.
  (6) Formation of a pigment: negative.
  (7) Urease: positive.
  (8) Oxidase: positive.
  (9) Catalase: positive.
  (10) Temperature and pH for growth: 20°–37° C., pH 6–8
  (11) Behavior to oxygen: aerobic.
  (12) O(oxidation) - F(fermentation) test: negative.
  (13) Acid formation from glucose: negative.
  (14) Decomposition of gelatin: negative.
  (15) Utilization of saccharide:
    D-glucose: negative.
    L-arabinose: negative.
    D-mannose: negative.
    D-mannitol: negative.
    maltose: negative.

The novel strain AK 201 was identified as belonging to the genus Alcaligenes, taking into account its bacteriological properties, i.e., it is an aerobic, gram negative, non-fermenting, motile bacillus having peripheral flagella and it is positive to oxidase and negative in the O(oxidation) - F(fermentation) test. The above bacteriological properties were measured according to the procedure as described in *Biseibutsu no Bunrui to Dotei* (Classification and Identification of Microorganisms) (1990) edited by Takeji Hasegawa and published by Gakkai Shuppan Center, Japan, "Aerobic Bacteria" written by Kazuo Komagata, and in The Procaryotes: A Handbook on Habitats, Isolation and Identification of Bacteria, (Ed.) M. P. Starr et al (1981). The identification of the bacterium was performed according to the procedure described in Bergey's Manual of Systematic Bacteriology, vol. 1 (1984).

The following Tables 2 to 4 show comparisons in bacteriological properties between the novel strain AK 201 and the known species belonging to the genus Alcaligenes.

a novel species of the genus Alcaligenes, which is different from the known species of the genus Alcaligenes.

The strain Ak 201 is characterized by effectively utilizing fats, oils and long chain fatty acids as a carbon source in growth and synthesis of a microbial polyester as described later. Therefore, the species to which strain AK 201 belongs, has been designated as *Alcaligenes lipolytica*.

Hereinbelow, the culturing conditions to be employed in the method of the present invention will be described, referring to *Alcaligenes lipolytica* AK 201 taken as an example of the strains to be cultured for the production of the desired microbial polyester in the present invention.

*Alcaligenes lipolytica* Ak 201 can be cultured under the conditions similar to those for other strains of the genus Alcaligenes. That is, it is generally cultured at a temperature of from 20° to 40° C., preferably from 24°

TABLE 2

Bacteriological Properties of Species Belonging to the Genus Alcaligenes

| | AK 201 | A. faecalis | A. denitrificans | A. eutrophus | A. paradoxus | A. latus |
|---|---|---|---|---|---|---|
| Width of cell > 1.2 μm | − | − | − | − | − | + |
| Formation of a cellular pigment of yellow carotenoid | − | − | − | − | + | − |
| Oxidase reaction | + | + | + | + | + | + |
| Reduction of a nitrate | − | − | + | + | ± | + |
| Denitrification reaction | − | + | + | + | − | − |
| Hydrolysis of gelatin | − | − | − | − | ± | + |
| Acid formation from glucose | − | − | − | | | |
| Utilization of carbon source | | | | | | |
| D-glucose | − | − | − | M* | + | + |
| L-arabinose | − | − | − | − | + | − |
| D-mannitol | − | − | − | − | + | − |

*M indicates that if it is a mutant, it is positive.

TABLE 3

Bacteriological Properties of Species Belonging to Genus Alcaligenes

| | AK 201 | A. faecalis | A. dentrificans | A. eutrophus | A. paradoxus | A. latus |
|---|---|---|---|---|---|---|
| Utilization of carbon source | | | | | | |
| D-mannosse | − | − | − | − | + | − |
| D-gluconic acid | − | − | + | + | + | + |
| acetic acid | + | + | + | + | + | − |
| adipic acid | + | − | + | + | + | − |
| Accumulation of PHB* | + | | + | + | + | + |
| Catalase | + | + | + | + | + | + |
| Urease | + | − | − | − | + | − |
| Hydrolysis of Tween 80 | + | − | − | − | − | + |
| Utilization of other carbon source | | | | | | |
| lactose | − | − | − | − | − | − |
| esculin | − | − | − | − | − | − |
| maltose | − | − | − | − | − | − |

*poly(3-hydroxybutyrate)

TABLE 4

Bacteriological Properties of Species Belonging to Genus Alcaligenes

| | AK 201 | A. faecalis | A. dentrificans | A. eutrophus | A. paradoxus | A. latus |
|---|---|---|---|---|---|---|
| Utilization of other carbon source | | | | | | |
| N-acetylglucosamine | − | − | − | | | |
| capric acid | + | + | ± | − | − | − |
| lactic acid | + | + | + | + | + | + |
| malic acid | + | + | + | + | + | + |
| citric acid | + | + | + | + | + | + |
| phenylacetic acid | + | + | ± | + | ± | + |
| alanine | + | + | + | + | + | + |
| arginine | − | − | − | | | − |
| tyrosine | + | ± | ± | ± | ± | ± |
| phenylalanine | + | + | + | + | + | − |

From the comparisons indicated in the above Tables 2–4, it is reasonably judged that the strain AK 201 is of to 33° C. The initial pH value for culturing is generally in the range of from 6.0 to 8.0, preferably from 6.2 to 7.5.

Various mediums, including synthetic, semi-synthetic and natural mediums, can be used as a liquid medium in the present invention.

When inorganic mediums indicated in Table 1 are employed, at least one carbon source for use in the growth of a strain belonging to the genus Alcaligenes for use in the present invention is added to the inorganic mediums. Representative examples of such carbon sources include saturated or ethylenically unsaturated straight chain fatty acids each having 2 to 22 carbon atoms; fats and oils, such as animal fats and vegetable oils; organic acids, such as citric acid, gluconic acid, succinic acid, glutaric acid, adipic acid, suberic acid and azelaic acid; alcohols, such as methanol, ethanol and glycerol; and aliphatic straight-chain hydrocarbons, such as n-octane and n-nonane.

The carbon source for use in the growth of a strain belonging to the genus Alcaligenes for use in the present invention may be selected independently of the carbon source for use in the synthesis of a polyester as described later. Among carbon sources, long chain fatty acids, fats and oils are effectively utilized for both the growth of the strain belonging to the genus Alcaligenes for use in the present invention and the synthesis of a polyester.

Moreover, various amino acids as well as organic nitrogen-containing nutrient sources, such as polypeptone, meat extract, casamino acid, yeast extract and molasses, can be used for the growth of the strain belonging to the genus Alcaligenes for use in the present invention.

As in conventional liquid mediums for use in the culturing of microorganisms, the liquid medium for use in the present invention contains a nitrogen source and inorganic ions.

Representative examples of nitrogen sources include inorganic ammonium salts, such as ammonium phosphate, ammonium sulfate and ammonium chloride, amino acids, organic nitrogen-containing nutrient sources as mentioned above, ammonium salts of organic acids, and amides from organic acids.

Representative examples of inorganic ions include ions of sodium, potassium, magnesium, calcium, chlorine, sulfate, phosphate, iron, manganese, zinc, copper and cobalt.

In the method of the present invention, it is requisite that the strain belonging to the genus Alcaligenes be fed with at least one carbon source (hereinafter referred to as "essential carbon source") for use in the synthesis of a microbial polyester comprising 3-hydroxybutyrate monomer units.

The essential carbon source is indispensable in the method of the present invention, and used for the synthesis of the microbial polyester or for both the synthesis of the microbial polyester and the growth of the strain belonging to the genus Alcaligenes. Accordingly, the essential carbon source performs a different function than the carbon source utilized only to grow the strain, but there are some molecules which can perform both functions.

In the method of the present invention, the essential carbon source is selected from the group consisting of fatty acids each having 10 to 22 carbon atoms, derivatives thereof, and mixtures of the fatty acids and the derivatives. The fatty acids may be saturated or ethylenically unsaturated. It is preferred that each of the fatty acids have 11 to 18 carbon atoms. The derivatives of the fatty acids include metal ($Na^+$, $K^+$, $Ca^{2+}$, $Mg^{2+}$, etc.) salts, ammonium salts, esters of fatty acids with an alkyl alcohol having 1 to 3 carbon atoms, mono- or diesters of fatty acids with an alkylene glycol having 2 or 3 carbon atoms, mono-, di- or triesters of fatty acids with glycerol, and amides of fatty acids of the formula $-CONH_2$. Further, the derivatives of the fatty acids include a fat or an oil comprised of a mixture of triglycerides of fatty acids each having 10 to 22 carbon atoms.

The concentration of the essential carbon source in the liquid medium for use in the present invention is not critical. However, it is generally in the range of from 0.5 to 50 g/liter, preferably from 1 to 10 g/liter.

Preferred examples of microbial polyesters produced by the method of the present invention are a homopolymer of a 3-hydroxybutyrate monomer, and a copolymer of a 3-hydroxybutyrate monomer and a 3-hydroxyvalerate monomer.

The microbial polyester produced by the method of the present invention generally has a number average molecular weight of from 50,000 to 2,000,000 and preferably from 100,000 to 1,000,000, as measured by gel permeation chromatography using monodispersed polystyrenes as reference material.

The structure of the produced microbial polyester depends on the molecular structure of the employed essential carbon source. For example, when a strain belonging to the genus Alcaligenes for use in the present invention is cultured on a single carbon source selected from the group consisting of fatty acids, the number of carbon atoms of which is even between 10 and 22 (hereinafter, such fatty acids are frequently referred to simply as "even fatty acids"), and derivatives thereof to thereby grow the strain and produce a microbial polyester, the produced microbial polyester is a homopolymer of a 3-hydroxybutyrate monomer. On the other hand, when the strain is cultured on a single carbon source selected from the group consisting of fatty acids, the number of carbon atoms of which is odd between 10 and 22 (hereinafter, such fatty acids are frequently referred to simply as "odd fatty acids"), and derivatives thereof to thereby grow the strain and produce a microbial polyester, the produced microbial polyester is a copolymer of a 3-hydroxybutyrate monomer and a 3-hydroxyvalerate monomer. Further, when the carbon source selected from even fatty acids and derivatives thereof is employed in combination with the carbon source selected from odd fatty acids and derivatives thereof, a copolymer of a 3-hydroxybutyrate monomer and a 3-hydroxyvalerate monomer is produced.

The structure of the produced microbial polyester depends not only on the molecular structure of the employed essential carbon source as mentioned above, but also on the molecular structure of an additional carbon source for use in the synthesis of the microbial polyester. For example, a copolymer of a 3-hydroxy butyrate monomer and a 3-hydroxyvalerate monomer is produced when a strain belonging to the genus Alcaligenes for use in the present invention is cultured in a mixture of an essential carbon source selected from the group consisting of fatty acids, the number of carbon atoms of which is even between 10 and 22, and derivatives thereof with at least one additional carbon source selected from the group consisting of compounds of the formula:

$$CH_3(CH_2)_{2n-1} X \qquad (I)$$

wherein X represents a group of the formula

in which R represents a hydroxyl group, a methoxy group or an ethoxy group, or a group of the formula —CH$_2$—OR', in which R' represents a hydrogen atom, an acetyl group or a propionyl group, and n is an integer of from 1 to 4.

In the method of the present invention, a strain belonging to the genus Alcaligenes for use in the present invention may be cultured according to either a one-stage culturing method or a two-stage culturing method.

In the one-stage culturing method, the strain is cultured in at least one carbon source selected from the group consisting of fatty acids each having 10 to 22 carbon atoms and derivatives thereof so as to grow the strain and simultaneously produce the microbial polyester. The culturing may be carried out in the presence of at least one additional carbon source mentioned above, which promotes the growth of the strain and/or controls the characteristics of the produced microbial polyester.

In the two-stage culturing method, the culturing in the first stage is conducted primarily or mainly to grow the strain. Grown cells of the strain are collected and introduced into a second-stage medium, and the second stage culturing is conducted primarily or mainly to produce the microbial polyester. That is, in the first stage, a carbon source which is suitable for the growth of the strain is chosen. In the second stage, at least one essential carbon source selected from the group consisting of fatty acids each having 10 to 22 carbon atoms and derivatives thereof is employed either independently or together with at least one additional carbon source described above. In the second stage, it is advantageous to carry out culturing either in a reduced amount of, or in the complete absence of at least one essential nutrient source, such as a nitrogen source and a phosphorus source, in order to restrict the growth of the strain and promote the production of the microbial polyester.

After the completion of culturing, the microbial polyester comprising 3-hydroxybutyrate monomer units is isolated from the cultured broth according to conventional methods.

In the method in which a one-stage culturing is performed, the cultured broth is directly subjected to treatments for isolation of the microbial polyester. For example, cells of the strain are collected, washed with distilled water, and lyophilized to obtain lyophilized cells. Subsequently, these cells are extracted, while heating, with a good solvent, such as chloroform, to obtain a polyester extract. The thus obtained extract is concentrated, and a poor solvent, such as methanol and hexane, is added thereto to precipitate a microbial polyester.

In the method in which a two-stage culturing is performed, cells of the strain are collected after a first-stage culturing, and introduced into a medium for use in a second-stage culturing. A second-stage culturing is performed. Thereafter, cells of the strain are treated in substantially the same manner as described above with respect to the method in which a one-stage culturing is performed.

The melting temperature, the heat of fusion and the glass transition temperature of the microbial polyester are measured by differential scanning calorimetry. The molecular weight and the molecular weight distribution of the microbial polyester are measured by gel filtration chromatography.

The composition of the microbial polyester is determined by gas chromatography. Lyophilized cells containing a microbial polyester or an isolated polyester is subjected to methanolysis to obtain methyl esters of monomers, which are sampled and injected in a gas chromatograph (see H. Brandl et al, Int. J. Biol. Macromol., 11, pages 49–55, 1989).

PREFERRED EMBODIMENT OF THE INVENTION

The present invention will be described in greater detail with reference to the Examples, which should not be construed to be limiting the scope of the present invention.

EXAMPLES 1–4

Alcaligenes lipolytica AK 201 is aseptically inoculated into a liquid medium placed in a Sakaguchi flask (a one-neck, square-shouldered flask developed and widely used in Japan to culture microorganisms in a liquid medium on a laboratory scale, which neck has at its one end an opening provided with a cotton stopper) having a volume of 500 ml. As the liquid medium, use is made of one prepared by adding a carbon source in a concentration of 3 g/liter to 100 ml of an inorganic medium having the composition indicated in Table 1 above. The carbon source is undecanoic acid in Example 1, pentadecanoic acid in Example 2, sodium stearate in Example 3 and rapeseed oil in Example 4. The cells in the inoculated liquid mediums are cultured at 30° C. for 48 hours while shaking at 130 strokes per minute.

After the completion of the culturing, the resultant cultured broths are individually centrifuged at 8,000 rpm for 15 minutes and washed with water, and the cells of Alcaligenes lipolytica AK 201 are collected. The collected cells are lyophilized to thereby obtain lyophilized cells. Polyester accumulated in the cells is extracted from the lyophilized cells by the use of 100 ml of hot chloroform to obtain an extract solution. The extract solution is concentrated to a concentration of about 5 ml, and hexane is added to cause a polyester to precipitate. The precipitated polyester is filtered off and dried to thereby obtain a dry polyester.

Table 5 shows the results of the biosynthesis of a polyester in Examples 1 to 4.

TABLE 5

| | | Results of Biosynthesis of Polyester | | | | | |
|---|---|---|---|---|---|---|---|
| Example | Carbon source | Weight of dry cells (g) per liter of cultured broth | Polyester content of dry cells (wt. %) | Composition (Mol %) 3HB | 3HV | Tm (°C.) | Mn×10$^{-4}$ |
| 1 | Undecanoic acid | 2.6 | 31 | 67 | 33 | 92 | 72 |
| 2 | Pentadecanoic acid | 2.4 | 58 | 78 | 22 | 106 | 58 |
| 3 | Sodium stea- | 2.3 | 30 | 100 | 0 | 172 | 52 |

TABLE 5-continued

Results of Biosynthesis of Polyester

| Example | Carbon source | Weight of dry cells (g) per liter of cultured broth | Polyester content of dry cells (wt. %) | Composition (Mol %) 3HB | Composition (Mol %) 3HV | Tm (°C.) | Mn×10⁻⁴ |
|---|---|---|---|---|---|---|---|
| 4 | rate rapeseed oil | 2.7 | 44 | 100 | 0 | 171 | 57 |

Note
Tm: Melting temperature
Mn: Number average molecular weight
3HB: 3-hydroxybutyrate
3HV: 3-hydroxyvalerate

EXAMPLES 5-7

*Alcaligenes lipolytica* AK 201 is inoculated into a liquid medium and cultured under substantially the same conditions as in Examples 1 to 4, except that lard (hog's fat) is used in Example 5, olive oil in Example 6 and ethyl laurate in Example 7 as a single carbon source. After culturing, obtained polyesters areanalyzed.

The results of the biosynthesis of a polyester in Examples 5 to 7 are shown in Table 6 below.

TABLE 6

Results of Polyester Biosynthesis

| Example | Carbon source | Weight of dry cells (g) per liter of cultured broth | Polyester content of dry cells (wt. %) | Composition (Mol %) 3HB | Composition (Mol %) 3HV | Tm (°C.) |
|---|---|---|---|---|---|---|
| 5 | Lard | 2.4 | 31 | 100 | 0 | 172 |
| 6 | Olive oil | 3.1 | 47 | 100 | 0 | 171 |
| 7 | Ethyl laurate | 2.5 | 26 | 100 | 0 | 173 |

Note the meanings of 3HB, 3HV and Tm are defined below Table 5

EXAMPLE 8

*Alcaligenes lipolytica* AK 201 is inoculated into a liquid medium and cultured for 72 hours under substantially the same conditions as in Examples 1 to 4, except that 2 g/liter rapeseed oil is used as an essential carbon source, with 1 g/liter sodium propionate used as an additional carbon source. The resultant polyester is analyzed. As a result of the analysis, it is found that the weight of dry cells is 1.9 g/liter of cultured broth, the polyester content of dry cells is 22% by weight, the polyester is comprised of 94 mol. % of 3-hydroxybutyrate monomer units and 6 mol. % of 3-hydroxyvalerate monomer units, and the melting temperature of the polyester is 153° C.

EXAMPLE 9

100 ml of a liquid medium obtained by dissolving 10 g of polypeptone, 5 g of meat extract, 10 g of yeast extract and 5 g of (NH₄)₂SO₄ in one liter of water, is put in a Sakaguchi flask having a volume of 500 ml, and aseptically inoculated with *Alcaligenes lipolytica* AK 201. The cells in the inoculated liquid medium are cultured at 30° C. for 24 hours while shaking. After the completion of the culturing, the resultant cultured broth is centrifuged at 8,000 rpm for 10 minutes to collect cells of *Alcaligenes lipolytica* AK 201. The collected cells are introduced into 100 ml of a second-stage liquid medium (a medium having the same inorganic medium composition as in Table 4 except that (NH₄)₂HPO₄ is not contained, wherein 3 g/liter sodium palmitate is incorporated as an essential carbon source and 2 g/liter n-nonyl acetate as an additional carbon source). The cells in the second-stage liquid medium are cultured at 30° C. for 48 hours while shaking. After culturing, a product polyester is analyzed. As a result, it is found that the weight of dry cells is 7.4 g/liter of cultured broth, the polyester content of dry cells is 46% by weight, the polyester is comprised of 87 mol. % of 3-hydroxybutyrate monomer units and 13 mol. % of 3-hydroxyvalerate monomer units, and the melting temperature of the polyester is 134° C.

COMPARATIVE EXAMPLE

To inorganic culture mediums each of 100 ml having the composition shown in Table 1 are respectively added 3 g/liter sodium palmitate (control), 3 g/liter sodium butyrate (comparative) and 1 g/liter sodium butyrate (comparative) as carbon sources. The pH value of each of the mixtures is adjusted to 7.0. The resultant liquid mediums are separately placed in Sakaguchi flasks having a volume of 500 ml, and aseptically inoculated with *Alcaligenes lipolytica* AK 201. The cells in the inoculated liquid mediums are cultured at 30° C. for 48 hours while shaking at 130 strokes per minute. After culturing, the resultant cultured broths are individually centrifuged at 8,000 rpm for 15 minutes. At this stage, it is found that in the cultured broth obtained using 3 g/l sodium butyrate, there are no grown cells of *Alcaligenes lipolytica* AK 201. From the other cultured broths, precipitates are individually obtained, which are washed with water, followed by harvesting of the cells. Subsequently, the harvested cells are lyophilized to obtain lyophilized cells. The polyesters accumulated in the cells are individually extracted from the lyophilized cells with 100 ml of hot chloroform. After extraction, the resultant extract solutions are individually concentrated to about 5 ml, and hexane is added to cause polyesters to precipitate. The precipitated polyesters are individually filtered off, and dried to obtain dry polyesters.

The results of the biosyntheses of polyesters are shown in Table 7.

TABLE 7

| Carbon source (g/l) | Weight of dry cells (g) per liter of cultured broth | Polyester content of dry cells (wt. %) | Composition (mol %) 3HB | Composition (mol %) 3HV | Tm (°C.) | Mn×10⁻⁴ |
|---|---|---|---|---|---|---|
| sodium palmitate, 3 g/l (control) | 3.2 | 53 | 100 | 0 | 174 | 59 |
| sodium butyrate, 3 g/l (comparative) | 0 | — | — | — | — | — |
| sodium butyrate, 1 g/l (comparative) | 0.4 | 16 | 100 | 0 | 176 | 16 |

Note the meanings of 3HB, 3HV and Tm are defined below Table 5

REFERENTIAL EXAMPLE

Each of the strains *Alcaligenes lipolytica* AK 201, *Alcaligenes eutrophus* (ATCC 17699), and *Alcaligenes latus* (ATCC 29713) is aseptically inoculated into a liquid medium placed in a Sakaguchi flask having a volume 500 ml. The above liquid medium is obtained by adding 3 g/liter corn oil as a carbon source to 100 ml of an inorganic culture medium having the composition shown in Table 1. The cells in the inoculated liquid mediums are cultured at 30° C. while shaking at 130 strokes per minute. The growth condition of cells of each of the strains is visually examined every 24 hours, and the culturing is terminated 120 hours after the start of the culturing.

As a result, it is found that a conversion of the cultured broth to a suspension, indicating the growth of cells, is observed from 24 hours after the start of the culturing with respect to the cultured broth in which *Alcaligenes lipolytica* AK 201 is cultured. On the other hand, such a conversion to a suspension is not observed until the termination of the culturing with respect to both the cultured broth in which *Alcaligenes eutrophus* has been cultured and the cultured broth in which *Alcaligenes latus* has been cultured. For confirmation, the cells collected after the culturing are subjected to centrifugation. It is found that cell precipitation occurs with respect to the cultured broth in which *Alcaligenes lipolytica* AK 201 has been cultured, whereas no cell precipitation occurs with respect to the other cultured broths. The weight of dry cells of *Alcaligenes lipolytica* AK 201 is 3.2 g per liter of cultured broth.

What is claimed is:

1. A method for producing a microbial polyester comprising D-(—)-3-hydroxybutyrate monomer units, which comprises the steps of:
   (1) providing a liquid medium containing at least one essential carbon source selected from the group consisting of fatty acids each having 10 to 22 carbon atoms and derivatives thereof;
   (2) culturing a strain belonging to the species *Alcaligenes lipolytica*, said strain producing a microbial polyester comprising D-(—)-3-hydroxybutyrate monomer units and being negative to both a nitrate reduction and a denitrification reaction, in said liquid medium, thereby obtaining a cultured broth containing a microbial polyester comprising D-(—)-3-hydroxybutyrate monomer units; and
   (3) isolating said microbial polyester from said cultured broth.

2. The method according to claim 1, wherein said microbial polyester is a homopolymer of a D-(—)-3-hydroxybutyrate monomer or a copolymer of a D-(—)-3-hydroxybutyrate monomer and a D-(—)-3-hydroxyvalerate monomer.

3. The method according to claim 1, wherein each of said fatty acids has 11 to 18 carbon atoms.

4. The method according to claim 2, wherein the number of carbon atoms of each fatty acid is odd to thereby produce a copolymer of a D-(—)-3-hydroxybutyrate monomer and D-(—)-3-hydroxyvalerate monomer.

5. The method according to claim 2, wherein the number of carbon atoms of each fatty acid is even.

6. The method according to claim 5, wherein said liquid medium further contains at least one additional carbon source selected from the group consisting of compounds of the formula:

$$CH_3(CH_2)_{2n-1}X \qquad (I)$$

wherein X represents a group of the formula

in which R represents a hydroxyl group, a methoxy group or an ethoxy group, or a group of the formula —CH$_2$—OR', in which R' represents a hydrogen atom, an acetyl group or a propionyl group, and n is an integer of from 1 to 4.

7. The method according to claim 1, wherein said strain utilizes at least one member selected from the group consisting of a fatty acid, a fat and an oil each having at least 10 carbon atoms.

* * * * *